United States Patent
Rao et al.

(10) Patent No.: US 10,274,424 B2
(45) Date of Patent: Apr. 30, 2019

(54) NON-APPROXIMATE VOIGT LINE PROFILE FITTING METHOD FOR ABSORPTION SPECTRUM SPECTROSCOPY

(71) Applicant: Space Engineering University, Beijing (CN)

(72) Inventors: Wei Rao, Beijing (CN); Guangyu Wang, Beijing (CN); Yanji Hong, Beijing (CN); Junling Song, Beijing (CN)

(73) Assignee: Space Engineering University, Beijing (CN)

( * ) Notice: Subject to any disclaimer, the term of this patent is extended or adjusted under 35 U.S.C. 154(b) by 0 days.

(21) Appl. No.: 15/959,179

(22) Filed: Apr. 21, 2018

(65) Prior Publication Data
US 2018/0238798 A1    Aug. 23, 2018

Related U.S. Application Data

(63) Continuation of application No. PCT/CN2016/098768, filed on Sep. 12, 2016.

(30) Foreign Application Priority Data

May 23, 2016   (CN) .......................... 2016 1 0346509

(51) Int. Cl.
*G01N 21/00*     (2006.01)
*G01N 21/39*     (2006.01)
(Continued)

(52) U.S. Cl.
CPC ................ *G01N 21/39* (2013.01); *G01J 3/42* (2013.01); *G01N 21/3504* (2013.01);
(Continued)

(58) Field of Classification Search
CPC .. G01J 2003/423; G01J 3/42; G01N 21/3504; G01N 21/39; G01N 33/0009; G01N 2201/0612; Y10T 436/25875
(Continued)

(56) References Cited

U.S. PATENT DOCUMENTS 7,433,806 B2   10/2008   Berk et al.
2003/0096425 A1*   5/2003   Berk ................... G01N 21/3504
436/171

(Continued)

FOREIGN PATENT DOCUMENTS

CN     1864053 A     11/2006

OTHER PUBLICATIONS

Zhou, Mo; A Detection Technique for Gas Concentration Based on the Spectral Line Shape Function; Spectroscopy and Spectral Analysis; vol. 35, No. 4, pp. 881-884, Apr. 2015.
(Continued)

*Primary Examiner* — Sunghee Y Gray
(74) *Attorney, Agent, or Firm* — Wayne & Ken, LLC; Tony Hom

(57) ABSTRACT

The present invention provides a Voigt line shape fitting method, including step 1: Calculate a Gauss line shape function and a Lorentz line shape function, and calculate a Voigt line shape function. Step 2: For determined line shape parameters to be fitted, calculate partial derivatives of the Voigt line shape function with respect to the parameters, convert a partial derivative of the Voigt line shape function with respect to a parameter into a partial derivative of the Gauss line shape function or the Lorentz line shape function with respect to the parameter. Step 3: Substitute the Voigt line shape function and the partial derivative of the Voigt line shape function with respect to the parameter to be fitted, into a least squares algorithm step, perform least squares
(Continued)

fitting calculation, and determine whether to terminate the least squares fitting calculation or return to step 1 to perform next iterative calculation.

1 Claim, 5 Drawing Sheets

(51) Int. Cl.
  *G01J 3/42* (2006.01)
  *G01N 21/3504* (2014.01)
(52) U.S. Cl.
  CPC .. *G01J 2003/423* (2013.01); *G01N 2021/399* (2013.01); *G01N 2201/0612* (2013.01); *G01N 2201/129* (2013.01)
(58) Field of Classification Search
  USPC .......... 356/432; 382/274; 73/23.37; 702/22; 703/2; 436/171, 181
  See application file for complete search history.

(56) References Cited

U.S. PATENT DOCUMENTS

| | | | | |
|---|---|---|---|---|
| 2009/0228245 | A1* | 9/2009 | Gilbert | G01N 30/8624 703/2 |
| 2010/0012843 | A1* | 1/2010 | Miller | G01N 21/39 250/339.07 |
| 2012/0185179 | A1* | 7/2012 | Zhou | G01N 21/3504 702/24 |
| 2014/0067282 | A1* | 3/2014 | Beyer | G01N 21/3504 702/24 |
| 2015/0301006 | A1 | 10/2015 | Quine et al. | |
| 2017/0191929 | A1* | 7/2017 | Berman | G01N 21/39 |

OTHER PUBLICATIONS

Marcus H. Mendenhall; Fast computation of Voigt functions via Fourier transforms; Journal of Quantitative Spectroscopy & Radiative Transfer 105 (2007) 519-524.

S.M. Abrarov; Rapidly convergent series for high-accuracy calculation of the Voigt function; Journal of Quantitative Spectroscopy & Radiative Transfer 111 (2010) 372-375.

A.B.Mc. Lean; Implementation of an efficient analytical approximation to the Voigt function for photoemission lineshape analysis; Journal of Electron Spectroscopy and Related Phenomena 69(1994) 125-132.

Zhang, Qingli; Double-peak Fitting of X-ray Diffraction by Voigt Profile Function; Journal of Synthetic Cry Stals; vol. 38, No. 2, Apr. 2009.

Jonas Westberg; Fast and non-approximate methodology for calculation of wavelength-modulated Voigt lineshape functions suitable for real-time curve fitting; Journal of Quantitative Spectroscopy & Radiative Transfer 113 (2012).

* cited by examiner

NON-APPROXIMATE VOIGT LINE PROFILE FITTING METHOD FOR ABSORPTION SPECTRUM SPECTROSCOPY

TECHNICAL FIELD

The present invention pertains to the field of optical flow field diagnosis, relates to diode laser absorption spectroscopy and a signal processing technology, and can be used to improve accuracy of measuring temperature, component concentration, and pressure by using TDLAS.

BACKGROUND

Currently, tunable diode laser absorption spectroscopy (TDLAS) is a very effective method for measuring parameters such as temperature, component concentration, velocity, or pressure in a combustion flow field. A basic principle of TDLAS is the Beer-Lambert law. By using properties of a laser absorption spectrum of gas molecules, intensity of laser light that penetrates absorbing gas is measured, and a light intensity absorption curve having a particular absorption line shape can be obtained. An absorption line shape function is directly related to field parameters. Values of the parameters can be obtained by performing line shape fitting on a measured absorption curve.

For a gas absorption environment, an absorption line shape is mainly decided by two physical mechanisms: Doppler broadening caused by thermal motion of molecules, and collision broadening caused by a collision between molecules. The two types of broadening respectively produce two corresponding line shape functions: a Gauss line shape function and a Lorentz line shape function. When gas pressure is low, Doppler broadening is dominant, and the absorption line shape is described by using a Gauss line shape. In a high pressure condition, molecules collide more frequently, collision broadening is dominant, and the absorption line shape is described by using a Lorentz shape. Actually, in most cases, there is no great difference between properties of the two types of broadening, and a Voigt line shape needs to be used to describe the absorption line shape. The Voigt line shape is expressed as a convolution of the Gauss line shape and the Lorentz line shape. This convolution expression does not have a definite analytical form. This causes two problems in applying a Voigt line shape function. This first problem is that a long calculation time is required for calculating a value of the Voigt line shape function in an integral form. The second problem is that the Voigt line shape function in the integral form cannot use a conventional line shape fitting tool to perform curve fitting, because a generic line shape fitting tool requires that an analytical expression should be used as an input parameter.

Currently, a general method for solving the two problems is approximating the analytical expression of the Voigt line shape to replace the original integral expression of the Voigt line shape. However, an approximate analytical expression also has its inherent disadvantage, that is, approximation inevitably causes an error. To reduce an error of approximation, an approximate analytical expression with high complexity or even a complex expression needs to be used. However, the complex approximate expression may also cause long-time calculation and non-convergence in line shape fitting. Therefore, for absorption spectrum measurement, a non-approximate Voigt line shape fitting method capable of fast calculation is of great significance.

The following documents and reports relate to calculation and fitting of a Voigt line shape function in laser absorption spectrum measurement.

1. "Rapidly convergent series for high-accuracy calculation of the Voigt function" (Journal of Quantitative Spectroscopy & Radiative Transfer 111 (2010) 372-375), a dissertation by S. M. Abrarov, etc., Yale University, U.S.A. An exponential function sequence based on Fourier expansion is provided for implementing high-accuracy approximation of a Voigt function. Calculation accuracy in this approximate method can reach $10^{-9}$. Although calculation in this method is obviously faster than an integral method, an approximate expression is in a form of a sum of sequences and is quite complex.

2. "Implementation of an efficient analytical approximation to the Voigt function for photoemission lineshape analysis" (Journal of Electron Spectroscopy and Related Phenomena 64 (1994) 125-132), a dissertation by A. B. McLean, Queen's University, Canada. A simple approximate expression of a Voigt function is provided. This expression includes a sum of four polynomials in a same form. Each polynomial includes four fixed parameter values. Featuring a simple form and a high calculation speed, this approximate expression is also applicable to line shape fitting, but accuracy of approximation is not high.

3. "Double-peak Fitting of X-ray Diffraction by Voigt Profile Function" (Journal of Synthetic Crystals, issue 2, volume 38, 2009), a dissertation by Zhang Qingli, Anhui Institute of Optics and Fine Mechanics, Chinese Academy of Sciences. A Gauss-Hermite numerical integration formula applicable to M nodes is used for approximating a Voigt line shape function, and a double-peak Voigt profile is fitted by using the approximate expression. A fitting result indicates that a convergence speed and stability thereof are both high. However, this article also points out that an increase of nodes may cause an increase of calculation load, and a calculation speed may be obviously reduced in a case of multiple numerical iterations.

4. "Fast and non-approximate methodology for calculation of wavelength-modulated Voigt lineshape functions suitable for real-time curve fitting" (Journal of Quantitative Spectroscopy & Radiative Transfer 113 (2012) 2049-2057), a dissertation by Jonas Westberg, Umea University, Sweden. A non-approximate method for calculation of wavelength-modulated Voigt line shape functions is provided. In the article, a fast Fourier transform method is used to calculate an expression related to a convolution. The article describes in detail how to obtain an nth-order modulation harmonic factor after Fourier broadening of a wavelength-modulated Voigt line shape function. There is no expression approximation in the whole calculation process, and calculation is fast. However, the article does not describe how to use the method to perform Voigt line shape fitting.

Complexity of accurate calculation of the Voigt line shape function and feasibility of non-approximate calculation are proved in the foregoing documents. However, research on fitting of the Voigt line shape function is still based on an approximate expression. Non-approximate Voigt line shape function calculation makes non-approximate Voigt line shape fitting possible. On this basis, a non-approximate Voigt line shape fitting method for absorption spectrum measurement is implemented in the present invention.

SUMMARY

An objective of the present invention is to provide a non-approximate Voigt line shape fitting method to improve accuracy of gas parameter measurement performed by using a TDLAS method. Based on a nonlinear least squares fitting method, the method uses an FFT method to calculate a Voigt line shape function and first-order partial derivatives of the function with respect to parameters to be fitted, and applies a calculation result in a least squares fitting algorithm. Therefore, non-approximation is implemented in the whole fitting process. The method solves various problems caused by approximate calculation of a Voigt line shape function in a long term. The method is applicable to all fields that can use TDLAS to measure flow field parameters, for example, measure temperature and component concentration in an engine plume, a scramjet engine isolator or a combustion chamber, and an internal combustion engine, optimize combustion efficiency in fields of thermal power generation and coal furnaces, monitor pollutants, etc.

The present invention describe a method for non-approximate calculation of a Voigt line shape function. An implementation solution is as follows:

(1) Separately calculate a normalized Gauss line shape function and a normalized Lorentz line shape function according to given line shape parameters such as a center wavelength, a Gauss line width, and a Lorentz line width.

(2) Separately calculate Fourier transforms of the Gauss line shape function and the Lorentz line shape function.

(3) By using Fourier transform properties of a convolution, obtain a Fourier transform of the Voigt line shape function, which is equal to a product of the Fourier transforms of the Gauss line shape function and the Lorentz line shape function.

(4) Obtain a normalized Voigt line shape function by using an inverse Fourier transform. The present invention provides a method for non-approximate calculation of first-order partial derivatives of a Voigt line shape function with respect to line shape parameters. An implementation solution is as follows:

(1) By using differential properties of a convolution, convert first-order partial derivatives of a Voigt line shape function with respect to line shape parameters into first-order partial derivatives of a Gauss line shape function or a Lorentz line shape function with respect to the line shape parameters.

(2) Calculate the first-order partial derivatives of the Gauss line shape function or the Lorentz line shape function with respect to the line shape parameters.

(3) By using Fourier transform properties of the convolution, calculate the first-order partial derivatives of the Voigt line shape function with respect to the line shape parameters.

The present invention improves a nonlinear least squares fitting algorithm, so that the algorithm is applicable to curve fitting without a definite analytical expression. An implementation solution is as follows:

(1) Set initial values of line shape parameters to be fitted, and calculate a Voigt line shape function and first-order partial derivatives of the Voigt line shape function by using the initial values.

(2) Calculate an optimum factor SSE by using the calculated Voigt line shape function and a measured profile.

(3) Construct a Hessian matrix and a gradient equation by using the calculated first-order partial derivatives of the Voigt line shape function, and obtain an increment of parameters to be fitted.

(4) Recalculate the Voigt line shape function and optimum factor SSE by using the updated parameters to be fitted.

(5) Compare the new optimum factor with the old optimum factor, and determine whether to terminate the calculation or repeat steps (1) to (4) until fitting differences converge to an acceptable small value.

DESCRIPTION OF EMBODIMENTS

Figure 1:
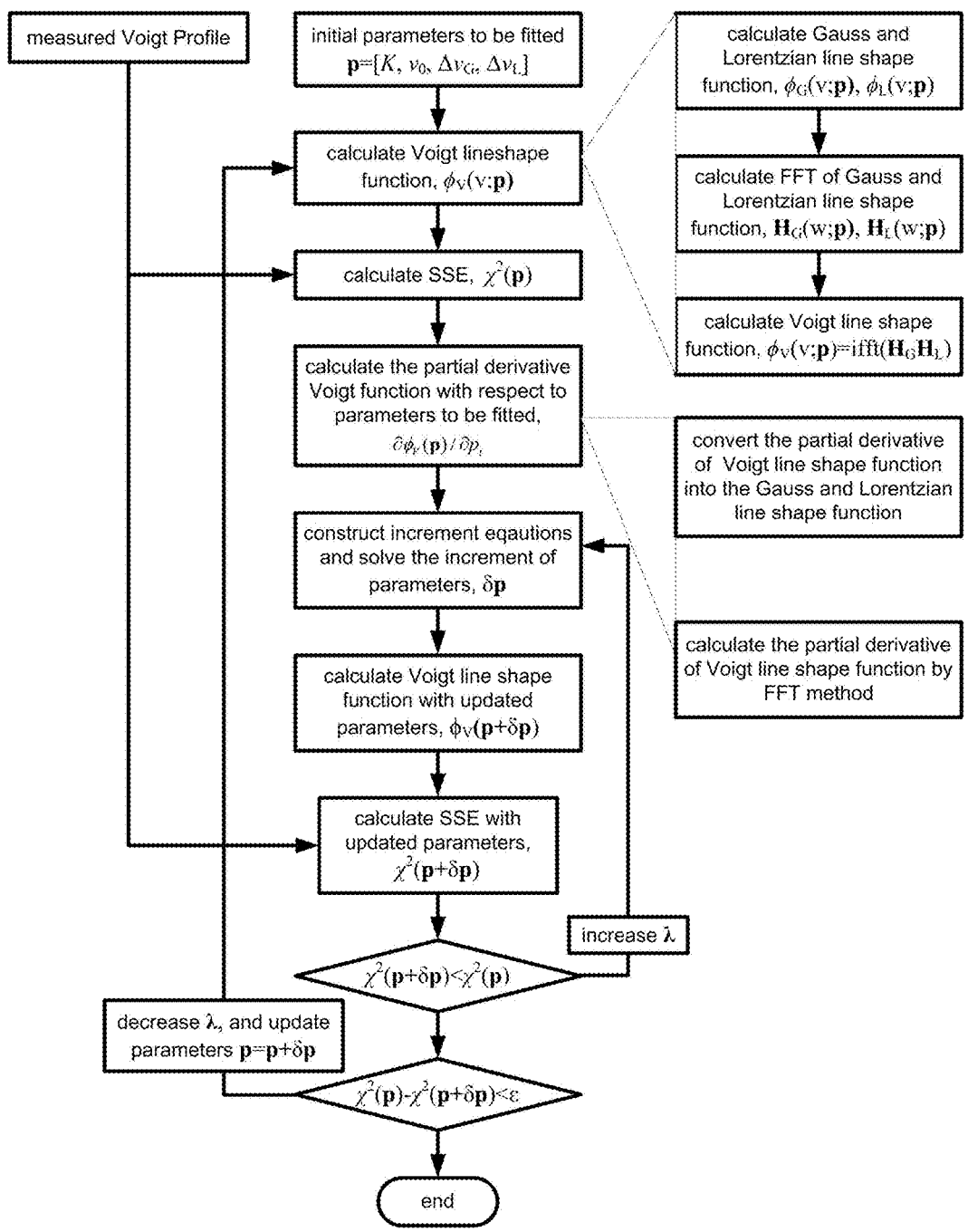
FIG. 1 is a principle flowchart of the method according to the present invention.

With reference to the accompanying drawings and embodiments, the following further describes in detail a non-approximate Voigt line shape fitting method for absorption spectrum measurement according to the present invention. FIG. 1 provides a principle flowchart of a non-approximate Voigt line shape fitting method according to the present invention.

An implementation solution of the present invention is as follows: The present invention provides a non-approximate Voigt line shape fitting method by fully using properties of convolution calculation and characteristics a Voigt line shape function in combination with actual application conditions for laser absorption spectrum measurement. The present invention includes three steps: a step of non-approximate calculation of a Voigt line shape function, a step of non-approximate calculation of first-order partial derivatives of the Voigt line shape function with respect to parameters, and a step of non-approximate least squares fitting of a Voigt line shape. A specific implementation solution is as follows:

Step 1: Non-Approximate Calculation of a Voigt Line Shape Function

The Voigt line shape function is in a form of a convolution of a Gauss line shape function and a Lorentz line shape function, and includes four line shape parameters in total: a center wavelength $v_0$, a Gauss line width $\Delta v_G$, a Lorentz line width $\Delta v_L$, and a line shape amplitude K. A Voigt line width may be obtained by using the Gauss line width and the Lorentz line width. In calculation of the Voigt line shape function, the four line shape parameters are known variables. Specific calculation steps are as follows:

(1) Calculate a normalized Gauss line shape function $\phi_G(v)$ and a normalized Lorentz line shape function $\phi_L(v)$, where the two line shape functions both have definite analytical expressions and are expressed as follows:

$$\phi_G(v) = \frac{2}{\Delta v_G} \sqrt{\frac{\ln 2}{\pi}} \exp\left[-4\ln 2\left(\frac{v}{\Delta v_G}\right)^2\right] \quad (1)$$

$$\phi_L(v) = \frac{2}{\pi} \frac{\Delta v_L}{4v^2 + \Delta v_L^2} \quad (2)$$

Correspondingly, an expression of the Voigt line shape function whose peak value is located at the center wavelength $v_0$ is:

$$\phi_V(v-v_0)=K\cdot\phi_G(v-v_0)\otimes\phi_L(v) \quad (3)$$

(2) Calculate Fourier transforms $H_G(\omega)$ and $H_L(\omega)$ of the normalized Gauss line shape function and the normalized Lorentz line shape function.

(3) By using Fourier transform properties of a convolution, obtain a Fourier transform $H_V(\omega)$ of the Voigt line shape function, which is equal to a product of the Fourier transforms of the Gauss line shape function and the Lorentz line shape function, that is, $$H_V(\omega)=H_G(\omega)H_L(\omega) \quad (4)$$

(4) Perform an inverse Fourier transform to obtain a normalized Voigt line shape function, and then multiply the normalized Voigt line shape function by a line shape amplitude K to obtain an actual Voigt line shape function $\phi_V(v)$.

Step 2: Non-Approximate Calculation of First-Order Partial Derivatives of the Voigt Line Shape Function with Respect to the Parameters The Voigt line shape function has four line shape parameters. Therefore, there are also four first-order partial derivatives of the Voigt line shape function with respect to the line shape parameters. A first-order partial derivative with respect to the line shape amplitude is a normalized Voigt line shape function. This is quite simple. The following mainly describes specific steps of calculating first-order partial derivatives with respect to the other three parameters.

(1) Using the center wavelength $v_0$ parameter as an example, obtain an expression of a first-order partial derivative of the Voigt line shape function with respect to the Gauss line width according to the equation (3):

$$\frac{\partial \phi_V(v-v_0)}{\partial v_0} = K\frac{\partial}{\partial v_0}\int_{-\infty}^{+\infty}\phi_G(u-v_0)\cdot\phi_L(v-u)du \quad (5)$$

By using differential properties of the convolution, the equation (5) may be expressed as:

$$\frac{\partial \phi_V(v-v_0)}{\partial v_0} = K\int_{-\infty}^{+\infty}\frac{\partial \phi_G(u-v_0)}{\partial v_0}\cdot\phi_L(v-u)du \quad (6)$$
$$= K\cdot\frac{\partial \phi_G(v-v_0)}{\partial v_0}\otimes\phi_L(v)$$

The equation (6) is still in a form of a convolution. The convolution includes two parts. The first part is a first-order partial derivative of the Gauss line shape function with respect to the center wavelength $v_0$. The second part is the Lorentz line shape function. Because the Gauss line shape function has the analytical expression (1), the first-order partial derivative may be expressed as follows by using the analytical expression:

$$\frac{\partial \phi_G(v-v_0)}{\partial v_0} = 8\ln2\frac{v-v_0}{\Delta v_G^2}\phi_G(v-v_0) \quad (7)$$

Therefore, a first-order partial derivative of the Voigt line shape function with respect to $v_0$, expressed in the equation (6), is a convolution of two analytical expressions. A Fourier transform method similar to that for calculating a Voigt function may be used for calculation.

(2) Calculate the first-order partial derivative $$\frac{\partial \phi_G(v-v_0)}{\partial v_0}$$

of the Gauss line shape function with respect to $v_0$ according to the equation (7).

(3) Calculate a Fourier transform of the first-order partial derivative of the Gauss line shape function with respect to $v_0$.

(4) By using the Fourier transform properties of the convolution, obtain a Fourier transform of the first-order partial derivative of the Voigt line shape function with respect to the center wavelength.

(5) Obtain the first-order partial derivative $$\frac{\partial \phi_V(v-v_0)}{\partial v_0}$$

of the Voigt line shape function with respect to $v_0$ through calculation by using an inverse Fourier transform.

(6) By using steps same as (1) to (5), calculate first-order partial derivatives $$\frac{\partial \phi_V(v-v_0)}{\partial \Delta v_G} \text{ and } \frac{\partial \phi_V(v-v_0)}{\partial \Delta v_L}$$

of the Voigt line shape function with respect to the Gauss line width and the Lorentz line width. Expressions of the two are in forms of convolutions:

$$\frac{\partial \phi_V(v-v_0)}{\partial \Delta v_G} = K\cdot\frac{\partial \phi_G(v-v_0)}{\partial \Delta v_G}\otimes\phi_L(v) \quad (8)$$

$$\frac{\partial \phi_V(v-v_0)}{\partial \Delta v_L} = K\cdot\phi_G(v-v_0)\otimes\frac{\partial \phi_L(v)}{\partial \Delta v_L} \quad (9)$$

Figure 2:
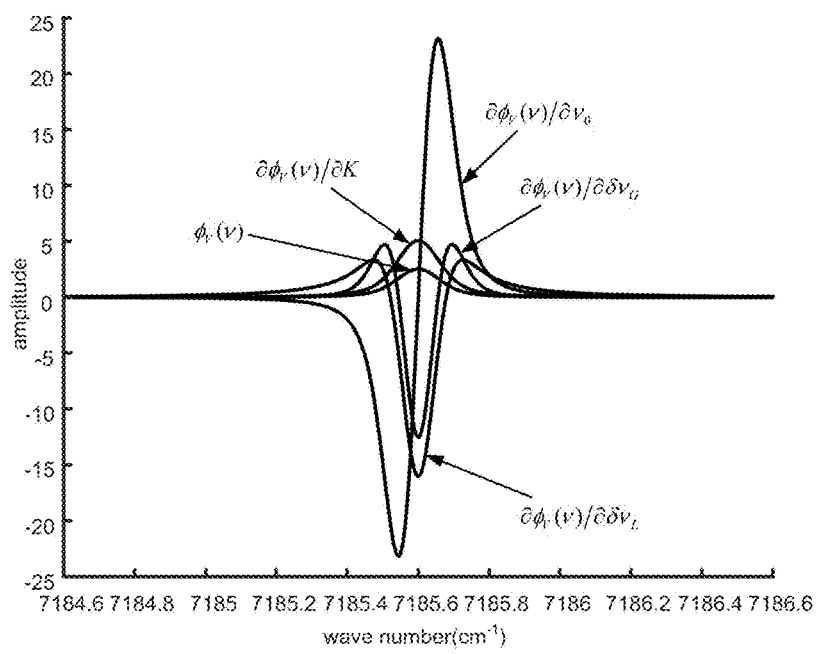
FIG. 2 shows a Voigt line shape function calculated by using the method according to the present invention, and calculated first-order partial derivatives of the Voigt line shape function with respect to line shape parameters.

FIG. 2 shows a typical Voigt line shape function and a first-order partial derivative of the Voigt line shape function with respect to each line shape parameter in laser absorption spectrum measurement, obtained by using the non-approximate calculation method.

Step 3: Non-Approximate Least Squares Fitting of a VOIGT Line Shape

The non-approximate least squares fitting of the Voigt line shape is an improvement over a typical Levenberg-Marquardt line shape fitting method for the Voigt line shape function. Least squares fitting is an iterative algorithm. Specific steps in each iterative cycle are as follows:

(1) Set an initial value of a line shape parameter vector $p=[K, v_0, \Delta v_G, \Delta v_L]$ to be fitted, and calculate the Voigt line shape function and a partial derivative of the Voigt line shape function with respect to each line shape parameter by using the initial value.

(2) Calculate an optimum factor $\chi^2(p)$ by using a measured profile and the calculated Voigt line shape function, where the optimum factor is expressed as follows by using a formula:

$$\chi^2(p) = \sum_{i=0}^{N-1} \left[ \frac{\phi_{V,i} - \phi_V(v_i; p)}{\sigma_i} \right]^2 \quad (10)$$

N is a quantity of measured data points; $\phi_{V,i}$ represents an $i^{th}$ piece of measurement data; and $\sigma_i$ represents a variance of the $i^{th}$ piece of measurement data, and may be set to 1 if its specific value is unknown.

(3) Calculate a first-order partial derivative of the optimum factor $\chi^2(p)$ with respect to a parameter to be fitted:

$$\frac{\partial \chi^2(p)}{\partial p_j} = 2\beta_j = -2 \sum_{i=0}^{N-1} \frac{[\phi_{V,i} - \phi_V(v_i; p)]}{\sigma_i^2} \frac{\partial \phi_V(v_i; p)}{p_j} \quad (11)$$

(11) indicates a partial derivative of the optimum factor with respect to an $i^{th}$ parameter to be fitted. For ease of subsequent description, $\beta_j$ is used to represent a summation term in the equation.

(4) Construct a Hessian matrix by using the calculated partial derivative of the Voigt line shape function with respect to each line shape parameter, where a formula for calculating an element $\alpha_{j,k}$ in the matrix is expressed as:

$$\alpha_{j,k} = \sum_{i=0}^{N-1} \frac{1}{\sigma_i^2} \left[ \frac{\partial \phi_V(v_i; p)}{p_j} \frac{\partial \phi_V(v_i; p)}{p_k} \right] \quad (11)$$

(5) Apply an offset to a diagonal element in the Hessian matrix by using a small least squares algorithm factor $\lambda$, and form a new matrix, where elements in the matrix are expressed as:

$$\alpha'_{j,j} = \alpha_{j,j}(1+\lambda)$$

$$\alpha'_{j,k} = \alpha_{j,k}(j \neq k) \quad (12)$$

(6) Solve the following line shape equation set to obtain an increment $\Delta p$ of parameters to be fitted:

$$\sum_{k=0}^{M-1} \alpha'_{j,k} \delta p_k = \beta_j \quad (13)$$

(7) With respect to the line shape parameters to be fitted and the obtained increment, repeat step (1) and step (2) to calculate a new optimum factor $\chi^2(p+\Delta p)$ by using the new line shape parameters.

(8) Compare the new optimum factor $\chi^2(p+\Delta p)$ with the old optimum $\chi^2(p)$, and determine whether to terminate the iterative cycle. If $\chi^2(p+\Delta p) > \chi^2(p)$, it indicates that the increment of parameters to be fitted makes an SSE between the Voigt profile and the measured profile worse, and the algorithm factor $\lambda$ needs to be increased. If $\chi^2(p+\Delta p) < \chi^2(p)$, first determine whether a difference between $\chi^2(p)$ and $\chi^2(p+\Delta p)$ is less than a convergence threshold $\varepsilon$. If $\chi^2(p) - \chi^2(p+\Delta p) < \varepsilon$, terminate the iterative cycle. Otherwise, replace p with p+$\Delta p$, decrease the algorithm factor $\lambda$, and repeat the iterative process.

Figure 3:
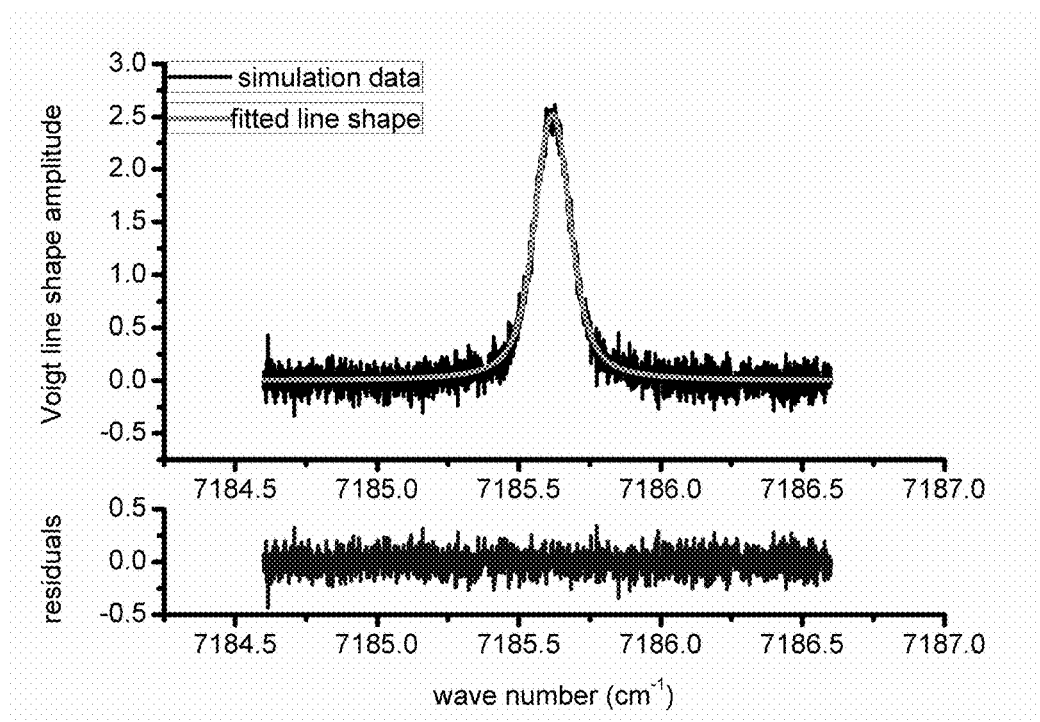
FIG. 3 shows a result of fitting simulation data by using the method according to the present invention.

FIG. 3 provides a result of Voigt line shape fitting performed by using the non-approximate Voigt line shape fitting method provided by the present invention, on absorption spectrum simulation data with a signal-to-noise ratio of 6 dB. An upper graph shows a fitted curve and simulation data. A lower graph shows a fitting error. It can be seen that the fitting error is within 3%.

Figure 4:
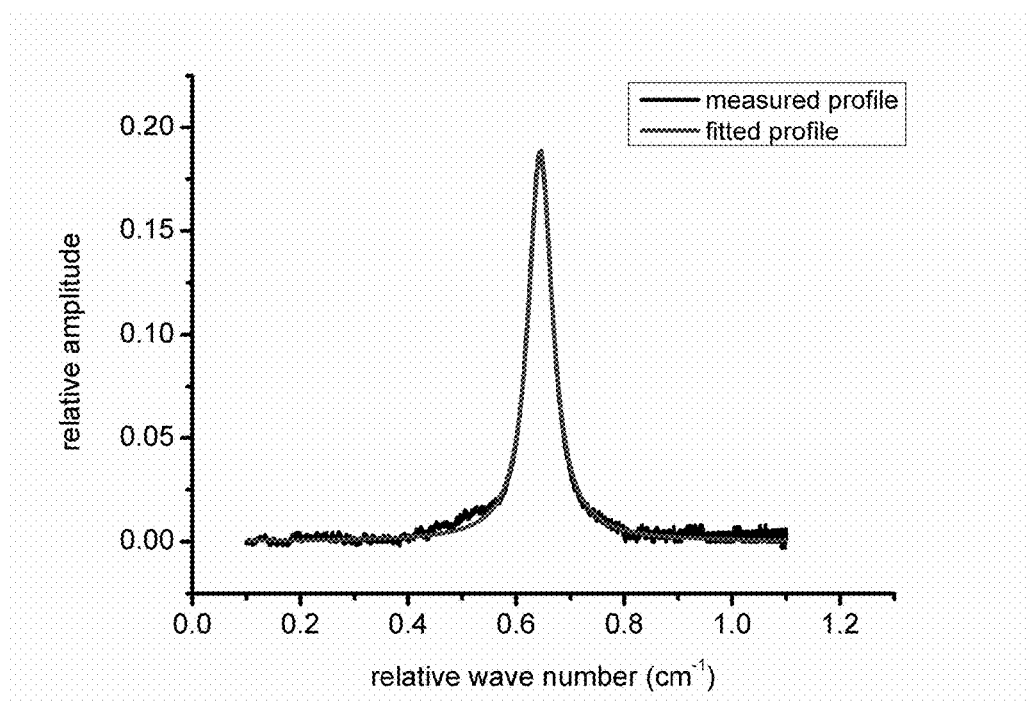
FIG. 4 shows a result of fitting measurement data by using the method according to the present invention.

FIG. 4 provides a result of Voigt line shape fitting performed by using the non-approximate Voigt line shape fitting method provided by the present invention, on actual absorption spectrum measurement data.

Figure 5:
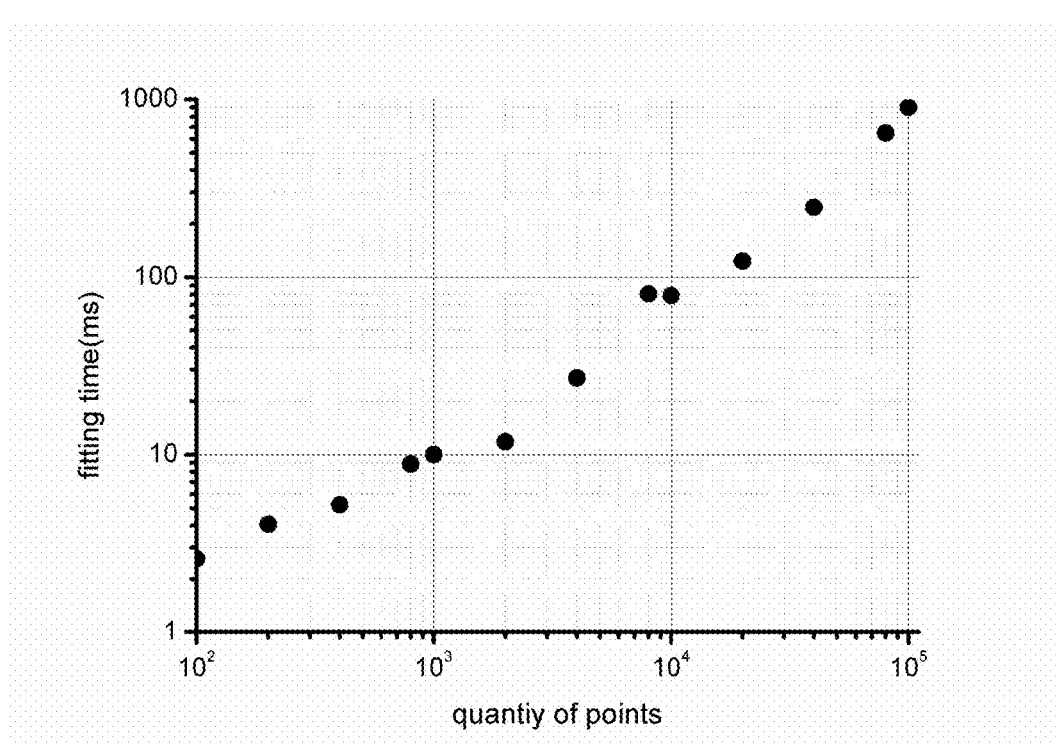
FIG. 5 shows a change curve of time consumed by calculation by using the method according to the present invention as a quantity of data points increases.

FIG. 5 provides a change relationship between time consumed in a non-approximate Voigt line shape fitting algorithm provided by the present invention and a quantity of fitted data points. It can be seen that, for 1000 data points, the whole fitting process needs to take only 10 ms.

What is claimed is:

1. A non-approximate Voigt line shape fitting method for absorption spectrum measurement in a tunable diode laser absorption spectroscopy (TDLAS), comprising the following steps:

step 1: performing a non-approximate calculation of a Voigt line shape function by:
(1) separately calculating a normalized Gauss line shape function and a normalized Lorentz line shape function according to given line shape parameters comprising a center wavelength, a Gauss line width, and a Lorentz line width;
(2) separately calculating Fourier transforms of the Gauss line shape function and the Lorentz line shape function;
(3) using Fourier transform properties of a convolution of a Gauss line shape function and a Lorentz line shape function, obtaining a Fourier transform of the Voigt line shape function, which is equal to a product of the Fourier transforms of the Gauss line shape function and the Lorentz line shape function; and
(4) obtaining a normalized Voigt line shape function by using an inverse Fourier transform;

step 2: performing a non-approximate calculation of first-order partial derivatives of the Voigt line shape function with respect to the parameters by:
(1) using differential properties of the convolution, converting the first-order partial derivatives of the Voigt line shape function with respect to the line shape parameters into first-order partial derivatives of the Gauss line shape function or the Lorentz line shape function with respect to the line shape parameters;
(2) calculating the first-order partial derivatives of the Gauss line shape function or the Lorentz line shape function with respect to the line shape parameters;
(3) using the Fourier transform properties of the convolution, calculating the first-order partial derivatives of the Voigt line shape function with respect to the line shape parameters;

step 3: performing a non-approximate least squares fitting of a Voigt line shape with respect to line shape parameters in laser absorption spectrum measurement by:
(1) setting initial values of line shape parameters to be fitted, and calculating the Voigt line shape function and first-order partial derivatives of the Voigt line shape function with respect to each line shape parameter by using the initial values;
(2) calculating an optimum factor by using the calculated Voigt line shape function and a measured profile;
(3) constructing a Hessian matrix and a gradient equation by using the calculated first-order partial derivatives of the Voigt line shape function, and obtaining an increment of parameters to be fitted;
(4) recalculating the Voigt line shape function and optimum factor by using the updated parameters to be fitted; and (5) comparing the new optimum factor with the old optimum factor, and determining whether to terminate the calculation or repeat steps (1) to (4) until fitting differences converge to an acceptable small value;

wherein the Voigt line shape is fitted to represent measurement of temperature, component concentration, velocity, and pressure of a gas under observation by the tunable diode laser absorption spectroscopy (TDLAS).

* * * * *